United States Patent [19]

Furlenmeier et al.

[11] Patent Number: 4,482,551
[45] Date of Patent: Nov. 13, 1984

[54] CEPHALOSPORIN DERIVATIVES

[75] Inventors: André Furlenmeier, Basel; Paul Lanz, Muttenz, both of Switzerland

[73] Assignee: Hoffmann-La Roche Inc., Nutley, N.J.

[21] Appl. No.: 403,951

[22] Filed: Jul. 30, 1982

Related U.S. Application Data

[63] Continuation of Ser. No. 163,114, Jun. 26, 1980, abandoned.

[51] Int. Cl.³ ................. A61K 31/545; C07D 501/56
[52] U.S. Cl. ..................................... 424/246; 544/27; 544/182
[58] Field of Search ........................... 544/27; 424/246

[56] References Cited

U.S. PATENT DOCUMENTS 4,278,793  7/1981  Durckheimer et al. ............. 544/27

Primary Examiner—Paul M. Coughlan, Jr.
Attorney, Agent, or Firm—Jon S. Saxe; Bernard S. Leon; Frank P. Hoffman

[57] ABSTRACT

There is presented compounds of the formula

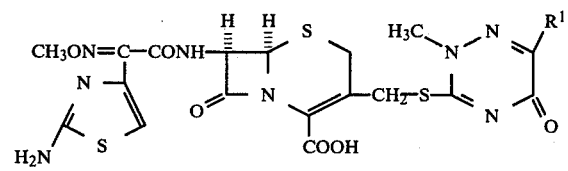

in which $R^1$ represents hydrogen or methyl, as well as readily hydrolyzable esters and salts of these compounds and the hydrates thereof.

Also presented are various intermediates and a process to produce the novel derivatives.

The acyl derivatives have pharmacological activity as antibacterial agents.

4 Claims, No Drawings

CEPHALOSPORIN DERIVATIVES

This is a continuation of application Ser. No. 163,114 filed June 26, 1980, now abandoned.

DESCRIPTION OF THE INVENTION

The present invention is concerned with novel cephalosporin derivatives, namely cephalosporin derivatives of the general formula

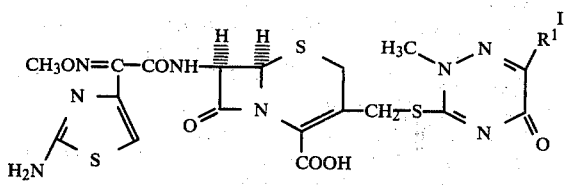

in which R¹ represents hydrogen or methyl, as well as readily hydrolysable esters and salts of these compounds and hydrates of the compounds of formula I or of their esters and salts.

As readily hydrolysable esters of the compounds of formula I there are to be understood compounds of formula I, the carboxy group of which is present in the form of a readily hydrolysable ester group. Examples of such esters, which can be of the conventional type, are the lower alkanoyloxyalkyl esters, e.g. the acetoxymethyl, pivaloyloxymethyl, 1-acetoxyethyl and 1-pivaloyloxyethyl ester; the lower alkoxycarbonyloxyalkyl esters, e.g. the methoxycarbonyloxymethyl, 1-ethoxycarbonyloxyethyl and 1-isopropoxycarbonyloxyethyl ester; the lactonyl esters e.g. the phthalidyl and thiophthalidyl ester; the lower alkoxymethyl esters, e.g. the methoxymethyl ester; and the lower alkanoylaminomethyl esters, e.g. the acetamidomethyl ester. Other esters, e.g. the benzyl and cyanomethyl esters, can also be useful.

Examples of salts of the compounds of formula I are alkali metal salts such as the sodium and potassium salt; the ammonium salt; alkaline earth metal salts such as the calcium salt; salts with organic bases such as salts with amines, e.g. salts with N-ethyl-piperidine, procaine, dibenzylamine, N,N'-dibenzylethylenediamine, alkylamines or dialkylamines, as well as salts with amino acids such as e.g. salts with arginine or lysine.

The compounds of formula I likewise form addition salts with organic or inorganic acids. Examples of such salts are hydrohalides, for example hydrochlorides, hydrobromides, hydroiodides, as well as other mineral acid salts such as sulphates, nitrates, phosphates and the like, alkyl- and monoaryl-sulphonates such as ethanesulphonates, toluenesulphonates, benzenesulphonates and the like and also other organic acid salts such as acetates, tartrates, maleates, citrates, benzoates, salicylates, ascorbates and the like.

The compounds of formula I (including their salts and readily hydrolysable esters) can be hydrated. The hydration can be effected in the course of the manufacturing process or can occur gradually as a result of hygroscopic properties of an initially anhydrous product.

The products in accordance with the invention can be present in the syn-isomeric form

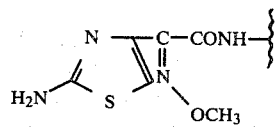

or in the anti-isomeric form

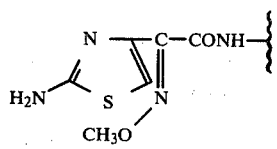

or as mixtures of these two forms. The syn-isomeric form or mixtures in which the syn-isomeric form predominates is/are preferred.

Preferred products are
(6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid,
(6R,7R)-7-[2-(2-amino-4-thiazolyl-2-[(Z)-methoxyimino]acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid and their salts as well as the corresponding hydrates.

The above acyl derivatives are manufactured in accordance with the invention in that (a) the protecting group R, opt. also a carboxy protecting group possibly present, in a compound of the general formula

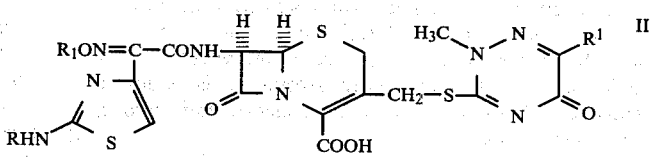

in which CH₃ has the significance given above, R represents a cleavable protecting group and the carboxy group can be present in protected form, is cleaved off, or in that (b) for the manufacture of a readily hydrolysable ester of a compound of formula I, a carboxylic acid of formula I is subjected to a corresponding esterification, or in that (c) for the manufacture of salts or hydrates of a compound of formula I or hydrates of these salts, a compound of formula I is converted into a salt or hydrate or into a hydrate of this salt.

If desired, the carboxy group present in the starting compound of formula II can be protected, e.g. by esterification to give a readily cleavable ester such as a silyl ester, e.g. the trimethylsilyl ester. The readily hydrolysable esters elucidated above also come into consideration. The carboxy group can also be protected by salt formation with an inorganic or tertiary organic base such as triethylamine. Possible R-protecting groups are, for example, acid-hydrolytically cleavable protecting groups such as e.g. t-butoxycarbonyl or trityl, or also basic-hydrolytically cleavable protecting groups such as e.g. trifluoroacetyl. Preferred R-protecting groups are chloro-, bromo- and iodoacetyl, especially chloroacetyl. The latter protecting groups can be cleaved off by treatment with thiourea.

The starting compounds of formula II can be manufactured e.g. by N-acylation of the corresponding 7-amino compound, namely by reacting a compound of the general formula

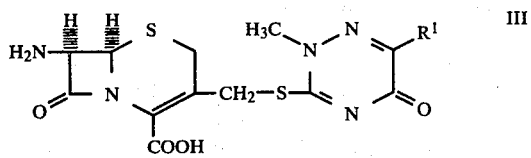

in which $R^1$ has the significance given above and the carboxy group and/or the amino group can be present in protected form, with an acid of the general formula

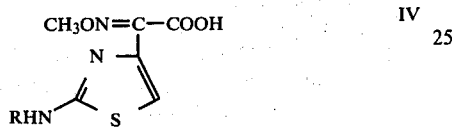

in which R has the significance given above, or with a reactive functional derivative of this acid and, if desired, cleaving off a carboxy protecting group possibly present.

If desired, the carboxy group present in the 7-amino compound of formula III can be protected, namely in the manner elucidated above for the starting compound of formula II to be manufactured. The amino group of the compound of formula III can be protected e.g. by a silyl protecting group such as trimethylsilyl.

As reactive functional derivatives of acids of formula IV there come into consideration e.g. halides, i.e. chlorides, bromides and fluorides; azides; anhydrides, especially mixed anhydrides with strong acids; reactive esters, e.g. N-hydroxysuccinimide esters, and amides, e.g. imidazolides.

The reaction of the 7-amino compound of formula III with the acid of formula IV or a reactive functional derivative thereof can be carried out in a manner known per se. Thus, e.g. a free acid of formula IV can be condensed with one of the mentioned esters corresponding to formula III by means of a carbodiimide such as dicyclohexylcarbodiimide in an inert solvent such as ethyl acetate, acetonitrile, dioxan, chloroform, methylene chloride, benzene or dimethylformamide and subsequently the ester group can be cleaved off. In place of carbodiimides there can also be used as the condensation agent oxazolium salts, e.g. N-ethyl-5-phenyl-isoxazolium-3'-sulphonate.

According to another embodiment, a salt of an acid of formula III, e.g. a trialkylammonium salt such as the triethylammonium salt, is reacted with a reactive functional derivative of an acid of formula IV as mentioned above in an inert solvent, e.g. one of the above-named.

According to a further embodiment, an acid halide, preferably the chloride, of an acid of formula IV is reacted with the amine of formula III. The reaction is preferably effected in the presence of an acid-binding agent, e.g. in the presence of aqueous alkali, preferably sodium hydroxide, or also in the presence of an alkali metal carbonate such as potassium carbonate or in the presence of a lower-alkylated amine such as triethylamine. As the solvent there is preferably used water, opt. in mixture with an inert organic solvent such as tetrahydrofuran or dioxan. The reaction can also be performed in an aprotic organic solvent such as e.g. dimethylformamide, dimethyl sulphoxide or hexamethylphosphoric acid triamide. With the use of silylated starting compounds of formula III the reaction is performed in anhydrous medium.

The reaction of the 7-amino compound of formula III with the acid of formula IV or a reactive functional derivative thereof can conveniently be effected at temperatures between about $-40°$ C. and room temperature, for example at about $0°-10°$ C.

The starting compounds of formula II can also be manufactured by thiolation, namely by reacting a compound of the general formula

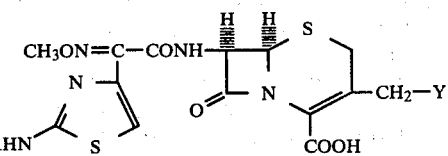

in which R has the significance given above, Y represents a leaving group and the carboxy group can be present in protected form, with a thiol of the general formula

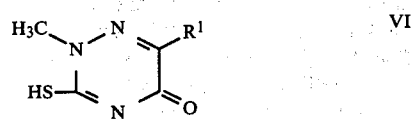

in which $R^1$ has the significance given above, and, if desired, cleaving off a carboxy protecting group possibly present.

As the leaving group Y of a compound of formula V there come into consideration, for example, halogens, e.g. chlorine, bromine or iodine, acyloxy residues, e.g. lower alkanoyloxy residues such as acetoxy, lower alkyl- or arylsulphonyloxy residues such as mesyloxy or tosyloxy, or the azido residue. The compound V can be protected at the carboxy group in the manner elucidated for the starting compound of formula II.

The reaction of the compound of formula V with the thiol of formula VI can be carried out in a manner known per se, e.g. at a temperature between about 40° and 80° C., conveniently at about 60° C., in a polar solvent, for example in an alcohol such as e.g. in a lower alkanol such as ethanol, propanol and the like, in dimethylformamide or dimethyl sulphoxide, preferably in water or in a buffer solution with a pH of about 6 to 7, preferably 6.5.

The thiols of formula VI stand in tautomeric equilibrium with the corresponding thiones. Their manufacture is described in Examples 1 and 2.

In accordance with process variant (a) of the process in accordance with the invention, the amino protecting group R of a starting compound of formula II is cleaved off. Protecting groups cleavable by acid hydrolysis are preferably removed with the aid of a lower alkanecarboxylic acid which opt. can be halogenated. In particular, formic acid or trifluoroacetic acid is used. The temperature is as a rule room temperature, although slightly higher or slightly lower temperature can be used, e.g. in the range of about 0° C. to +40° C. Protecting groups cleavable alkalinically are generally hydrolysed with dilute aqueous caustic alkali at 0° C. to 30° C. The chloroacetyl, bromoacetyl and iodoacetyl protecting groups can be cleaved off by means of thiourea in acidic, neutral or alkaline medium at about 0°-30° C. Hydrogenolytic cleavage (e.g. cleavage of benzyl) is unsuitable in this case, since the oxime function is reduced to the amino group during the hydrogenolysis.

After carrying our process variant (a), a carboxy protecting group possibly present in the reaction product can be cleaved off if desired. When the protecting group represents a silyl group (silyl ester), this group can be cleaved off especially readily by treatment of the reaction product with water. Lower alkanoyloxyalkyl, alkoxycarbonyloxyalkyl, lactonyl, alkoxymethyl and alkanoylaminomethyl esters are preferably cleaved enzymatically with the aid of a suitable esterase (at about 20°-40° C.). When the carboxy group is protected by salt formation (e.g. with triethylamine), then the cleavage of this salt-forming protecting group can be effected by treatment with acid. As the acid there can hereby be used e.g. hydrochloric acid, sulphuric acid, phosphoric acid or citric acid.

The carboxy protecting group can be cleaved off in the same manner as just described also before the cleavage of the protecting group R.

For the manufacture of the readily hydrolysable esters of the carboxylic acids of formula I in accordance with variant (b), the carboxylic acid is preferably reacted with the corresponding halide containing the ester group, preferably with the iodide. The reaction can be accelerated with the aid of a base, e.g. an alkali metal hydroxide or carbonate or an organic amine such as triethylamine. The esterification reaction is preferably carried out in an inert organic solvent such as dimethylacetamide, hexamethylphosphoric acid triamide, dimethyl sulphoxide or preferably, dimethylformamide. The temperature preferably lies in the range of about 0°-40° C.

The manufacture of the salts and hydrates of the compounds of formula I or the hydrates of these salts can be effected in a manner known per se, e.g. by reaction of the carboxylic acid of formula I with an equivalent amount of the desired base, conveniently in a solvent such as water or in an organic solvent such as ethanol, methanol, acetone and many others. The temperature of the salt formation is not critical. It lies in general at room temperature, but can also be slightly thereover or thereunder, about in the range of 0° C. to +50° C.

The manufacture of the hydrates for the most part takes place automatically in the course of the manufacturing process or as a result of hygroscopic properties of an initially anhydrous product. For the controlled manufacture of a hydrate, a completely or partially anhydrous product (carboxylic acid of formula I or ester, ether or salt thereof) can be exposed to a moist atmosphere, e.g. at about +10° C. to +40° C.

The 7-amino compounds of formula III used above can be manufactured starting from a compound of the formula

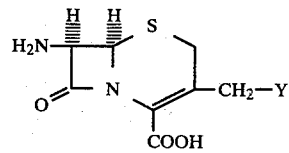

VII in which Y represents a leaving group and the carboxy group can be present in protected form, with a thiol of formula VI. The reaction can be effected under the same conditions as those which have been described for the reaction of the starting compounds V with VI. On the other hand, the compounds of formula V can be manufactured starting from a compound of formula VII and an acid of formula IV or a reactive functional derivative thereof under the same conditions as have been described for the reaction of the compounds of formulae III and IV.

A possibly obtained syn/anti mixture of a compound of formula I can be separated into the corresponding syn- and anti-forms in the customary manner, for example by recrystallisation or by chromatographical methods with the use of a suitable solvent or solvent mixture.

The compounds of formula I and II as well as the corresponding readily hydrolysable esters and salts or the hydrates of these products are antibiotically, especially bactericidally, active. They possess a broad spectrum of action against gram-positive bacteria, e.g. Staphylococci, and against gram-negative bacteria such as e.g. *Haemophilus influenzae, Neisseria gonorrhoeae*, as well as against various β-lactamase-forming gram-negative germs such as *Escherichia coli, Serratia marcescens, Pseudomonas aeruginosa, Proteus mirabilis, Proteus vulgaris*.

The compounds of formula I and II as well as the corresponding readily hydrolysable esters and salts or the hydrates of these products can be used for the treatment and prophylaxis of infectious diseases. A daily dosage of about 0.1 g to about 2 g comes into consideration for adults. The parenteral administration of the compounds in accordance with the invention is especially preferred.

For the demonstration of the antimicrobial activity of the mentioned products, the following representative representatives were tested:

Product A:
(6R,7R)-7-[2-(2-amino-5-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid sodium salt Product B:
(6R,7R)-7-[2-(2-amino-4-thiazolyl-2-[(Z)-methoxyimino]acetamido]-3-[[(2,5-dihydro-2,6-dimethyl-5-oxo-as-triazin-3-yl)thio]methyl]-8-oxo-5-thia-1-azabicyclo[4.2.0]oct-2-ene-2-carboxylic acid sodium salt.

| Activity in vitro: Minimum inhibitory concentration (μg/ml) | | |
| --- | --- | --- |
| Pathogenic agent | A | B |
| *Escherichia coli** | 0.04 | 0.08 |
| *Serratia marcescens** | 0.16 | 0.32 |
| *Enterobacter cloacae** | 2.5 | 2.5 |
| *Proteus mirabilis** | 0.04 | 0.08 |
| *Proteus vulgaris** | 0.02 | 0.02 |
| *Pseudomonas aeruginosa* | | |
| strain 1* | 40 | 80 |

-continued

| Activity in vitro: Minimum inhibitory concentration (μg/ml) | | |
| --- | --- | --- |
| Pathogenic agent | A | B |
| strain 2* | 40 | 80 |
| Haemophilus influenzae | 0.02 | 0.02 |
| Neisseria gonorrhoeae | 0.02 | 0.02 |
| Staphylococcus aureus | 2.5 | 2.5 |

*β-lactamase forming strain

| | Toxicity | |
| --- | --- | --- |
| Test substance | A | B |
| LD$_{100}$, mg/kg i.v. | 1000 | 500 |
| s.c. | >5000 | >4000 |
| p.o. | >5000 | >5000 |

The products in accordance with the invention can find use as medicaments e.g. in the form of pharmaceutical preparations which contain them or their salts in mixture with a pharmaceutical, organic or inorganic inert carrier material suitable for enteral or parenteral application, such as e.g. water, gelatin, gum arabic, lactose, starch, magnesium stearate, talc, vegetable oils, polyalkylene glycols, Vaseline, etc. The pharmaceutical preparations can be present in solid form, e.g. as tablets, dragées, suppositories, capsules; or in liquid form, e.g. as solutions, suspensions or emulsions. If necessary, they are sterilised and/or contain adjuvants such as preserving, stabilising, wetting or emulsifying agents, salts for the variation of the osmotic pressure, anaesthetics or buffers. The can also contain still other therapeutically valuable substances. The compounds of formula I and their salts or hydrates come into consideration preferably for parenteral application and for this purpose are preferably prepared as lyophilisates or dry powders for dilution with customary agents such as water or isotonic sodium chloride solution. The readily hydrolysable esters of the compounds of formula I and their salts or hydrates also come into consideration for enteral administration.

In the following working Examples all temperatures are given in °Centigrade.

EXAMPLE 1

(6R,7R)-7-[2-(2-amino-4-thiazolyl)-2-[(Z)-methoxyimino]-acetamido]-3-[[(2,5-dihydro-2-methyl-5-oxo-as-triazin-3-yl)thio]methyl]-8-oxo-5-thia-1-azabicyclo[4.2.-0]oct-2-ene-2-carboxylic acid sodium salt 61 g of (6R,7R)-7-[2-(chloroacetamido-4-thiazolyl)-2-[(Z)-methoxyimino]-acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid are treated in 1.5 l of water with 30.4 g of thiourea and, with nitrogen gasification and stirring, held for 20 hours at a pH-value of 7.0 with 1N sodium hydroxide via autotitrator. The pH-value is adjusted to 3.75 by dropwise addition of 1N HCl while stirring. The separated precipitate is filtered off under suction and rejected. Now, the filtrate is adjusted to a pH-value of 3.0 with 1N hydrochloric acid while stirring, the precipitate is filtered off under suction, washed with water, ethanol and petroleum ether and dried. The crude product obtained is suspended in 90 ml of acetone/water (1:1), treated with 45 ml of a 2N solution of sodium 2-ethylcaproate in ethyl acetate, stirred up to complete solution and thereafter precipitated with dropwise addition into 800 ml of acetone while stirring. The sodium salt is filtered off under suction, washed with acetone, ether and petroleum ether and dried. For further purification, the substance is dissolved in 800 ml of methanol while stirring and filtered off from a little undissolved substance. The filtrate is treated with active charcoal, filtered, evaporated to ca 400 ml in vacuo and filtered off from a little precipitated substance. The filtrate is precipitated with dropwise addition of 1.6 l of ethyl acetate, filtered off under suction, washed with ethyl acetate, ether and petroleum ether and dried. There is obtained (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-carboxylic acid sodium salt; m.p.=from 192° slow dec. $[\alpha]_D^{25} = -135°$ (c=1 in water).

The (6R,7R)-7-[2-(chloroacetamido-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid used as the starting substance can be manufactured as follows:

2-Methyl-5-oxo-3-thioxo-2,3,4,5-as-triazine 84 g of 2-methyl-thiosemicarbazide are introduced portionwise into a solution of 80.8 g of glyoxylic acid hydrate in 450 ml of dimethylformamide. The suspension is stirred at 80° for 45 minutes. The reaction mixture is cooled, treated with 2.5 l of water and the suspension is stirred at 0° for 1 hour. After filtration under suction, washing with water and drying, there is obtained the 2-methyl-thiosemicarbazone of glyoxylic acid, m.p. 204°–205° (dec.). This substance is introduced while stirring into a solution of 74 g of sodium carbonate in 700 ml of water and thereafter heated at 95°–98° for 3 hours while stirring. The solution is cooled to 5° and adjusted to a pH-value of 2 with stirring and dropwise addition of conc. hydrochloric acid. After suction filtration, washing with ice/water and drying, there is obtained 2-methyl-5-oxo-3-thioxo-2,3,4,5-as-triazine, m.p. 221°–222°.

(6R,7R)-7-amino-3-[[(2,5-dihydro-2-methyl-5-oxo-as-triazin-3-yl)thio]methyl]-8-oxo-5-thia-1-azabicyclo[4.2.-0]oct-2-ene-2-carboxylic acid 27.2 g of 7-amino-cephalosporanic acid are treated in 200 ml of water while stirring first of all portionwise with 23.1 g of sodium hydrogen carbonate and thereafter with 21.5 g of 2-methyl-5-oxo-3-thioxo-2,3,4,5-as-triazine. Subsequently, the mixture is heated at 60° for 5 hours with nitrogen gasification. The solution is cooled to 5°, adjusted to a pH-value of 3.5 with conc. hydrochloric acid, the precipitated substance is filtered off, washed with water and stirred twice with 230 ml of methanol each time, filtered off, washed with methanol and ether and dried in vacuo. There is obtained (6R,7R)-7-amino-3-[[(2,5-dihydro-2-methyl-5-oxo-as-triazin-3-yl)thio]methyl]-8-oxo-5-thia-1-azabicyclo[4.2.-0]oct-2-ene-2-carboxylic acid, m.p. from 195° dec., which is further reacted without further purification.

(6R,7R)-7-[2-(chloroacetamido-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid 63 ml of N,N'-dimethylformamide are added dropwise to a −20° cold suspension of 34.5 g of phosphorus pentachloride in 500 ml of dichloromethane, the mixture is stirred at −15° for 10 minutes, thereafter cooled to −25°, treated with 46 g of 2-(2-chloroacetamido-4-thiazolyl)-2-methoxyimino-acetic acid (syn-form) and stirred at −15° for 45 minutes. The solution is cooled to −30°, mixed with 50 g of ice, whereby the temperature rises to −15°.

The mixture is stirred at −15° for 10 minutes and then the dichloromethane solution is separated off. It is cooled to −15° and employed immediately for the following acylation.

Meanwhile, 61 g of (6R,7R)-7-amino-3-[[2,5-dihydro-2-methyl-5-oxo-as-triazin-3-yl)thio]methyl]-8-oxo-5-thia-1-azabicyclo[4.2.0]oct-2-ene-2-carboxylic acid are dissolved in 800 ml of water at a pH-value of 7.8 via autotitrator by dropwise addition of 2N sodium hydroxide while stirring and cooled to 0°. At this temperature there is added dropwise within 45 minutes the above −15° cold dichloromethane solution of the acid chloride and a pH-value of 7.8–8.0 is maintained by simultaneous dropwise addition of 2N sodium hydroxide via autotitrator. The mixture is subsequently stirred for a further 30 minutes at 5° and for 1 hour at 20°. The solution is treated with 500 ml of n-butanol and 500 ml of dichloromethane, whereafter it is adjusted to a pH-value of 7 with citric acid, stirred for 5 minutes at this pH-value and subsequently filtered in vacuo. The organic phase is separated, washed 3 times with 200 ml of water each time, treated with active charcoal, filtered off and evaporated in vacuo at 55° to ca 200 ml. The suspension obtained is cooled to 20° and filtered in vacuo. There is obtained a 1st fraction of solid (6R,7R-)-7-[2-(chloroacetamido-4-thiazolyl)-2-[(Z)-methoxyimino]-acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid. The mother liquor is evaporated to 100 ml in vacuo, mixed with 100 ml of ether and yields, after suction filtration, a 2nd fraction of the mentioned acid. Both fractions are dissolved together in 2 l of acetone while stirring within 15 minutes and filtered off from insolubles. 300 ml of butyl acetate are added to the filtrate and the acetone is distilled off in vacuo until the substance crystallises. There is obtained (6R,7R)-7-[2-(chloroacetamido-4-thiazolyl)-2-[(Z)-methoxyimino]-acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid, m.p. from 173° dec., $[\alpha]_D^{25} = -238.7°$ (c=1 in dimethylformamide). The product is uniform in accordance with thin-layer chromatography in the system n-propanol/acetic acid/water 55/15/30 and is further reacted without further purification.

EXAMPLE 2

(6R,7R)-7-[2-(2-amino-4-thiazolyl-2-[(Z)-methoxyimino]acetamido]-3-[[(2,5-dihydro-2,6-dimethyl-5-oxo-as-triazin-3-yl)thio]methyl]-8-oxo-5-thia-1-azabicyclo[4.2.0]oct-2-ene-2-carboxylic acid sodium salt 37 g of (6R,7R)-7-[2-(chloroacetamido-4-thiazolyl)-2-[(Z)-methoxyimino]-acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid and 18 g of thiourea are suspended in 800 ml of water and held at a pH-value of 7.0 for 20 hours with 1N sodium hydroxide via autotitrator with nitrogen gasification and stirring. The pH-value is adjusted to 4.0 by dropwise addition of 1N HCl while stirring and separated sludge is filtered off. Further 1N hydrochloric acid is added dropwise to the filtrate up to a pH-value of 2.8. The precipitate is filtered off under suction, washed with water, ethanol, ether and petroleum ether and dried. The substance is suspended in 30 ml of water, brought into solution by addition of 30 ml of a 2N solution of sodium 2-ethylcaproate and the solution is precipitated in 500 ml of acetone with dropwise addition and stirring. The sodium salt is filtered off under suction, washed with acetone, ether and petroleum ether and re-precipitated a further twice from water/acetone. This product is dissolved with 80 percent aqueous ethanol, filtered, concentrated in vacuo, evaporated several times with ethanol/butyl acetate, filtered off under suction and finally re-precipitated further from methanol/butyl acetate. There is obtained (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid sodium salt, m.p. from 180° dec., $[\alpha]_D^{25} = -164°$ (c=1 in water).

The (6R,7R)-6-[2-(chloroacetamido-4-thiazolyl)-2-[(Z)-methoxyimino]-acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid used as the starting compound can be manufactured as follows:

2,6-Dimethyl-5-oxo-3-thioxo-2,3,4,5-as-triazine 30 ml of pyruvic acid are dissolved in a solution of 42.4 g of sodium bicarbonate and 500 ml of water, treated with 42 g of 2-methyl-thiosemicarbazide and stirred at 95° for 2 hours. Conc. hydrochloric acid is slowly added dropwise to the cooled solution while stirring until a pH-value of 3.8 is reached. The precipitated substance is filtered off under suction, washed with water and recrystallised from methanol/water. There is obtained 2,6-dimethyl-5-oxo-3-thioxo-2,3,4,5-as-triazine, m.p. = 162°–164°.

(6R,7R)-7-amino-3-[[(2,5-dihydro-2,6-dimethyl-5-oxo-as-triazin-3-yl)thio]methyl]-8-oxo-5-thia-1-azabicyclo[4.2.0]oct-2-ene-2-carboxylic acid 27.2 g of 7-amino-cephalosporanic acid are dissolved in 200 ml of water at pH 7.0 by addition of 1N sodium hydroxide via autotitrator while stirring. Thereto there are added 18.9 g of 2,6-dimethyl-5-oxo-3-thioxo-2,3,4,5-as-triazine and the mixture is adjusted to a pH-value of 6.75 with 1N sodium hydroxide. Thereafter, the mixture is heated at 55° for 5 hours under nitrogen gasification. The solution, cooled to 5°, is adjusted to a pH-value of 3.8 with 3N hydrochloric acid while stirring, the precipitated substance is filtered off under suction, washed with water and acetone and dried. For the purification, the powdered substance is suspended several times in methane, filtered off, washed with methanol and ether and dried. There is obtained (6R,7R)-7-amino-3-[[(2,5-dihydro-2,6-dimethyl-5-oxo-as-triazin-3-yl)thio]methyl]-8-oxo-5-thia-1-azabicyclo[4.2.0]oct-2-ene-2-carboxylic acid; m.p. from 190° slow dec. The substance is further reacted without further purification.

(6R,7R)-7-[2-(chloroacetamido-4-thiazolyl)-2-[(Z)-methoxyimino]-acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid 41.8 ml of N,N'-dimethylacetamide are added dropwise to a −20° cold suspension of 22.7 g of phosphorus pentachloride in 400 ml of dichloromethane, the mixture is stirred at −15° for 10 minutes, thereafter cooled to −25°, treated with 30.4 g of 2-(2-chloroacetamido-4-thiazolyl)-2-methoxyimino-acetic acid (syn-form) and stirred at −15° for 45 minutes. Thereafter, the solution is cooled to −30°, mixed with 40 g of ice, whereby the temperature rises to −15°. The mixture is further stirred at −15° for 10 minutes, then the dichloromethane solution is separated off, it is cooled to −15° and it is used immediately for the following acylation.

Meanwhile, 41.8 g of (6R,7R)-7-amino-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid are dissolved in 600 ml of water at a pH-value of 7.8 via autotitrator by dropwise addition of 2N sodium hydroxide while stirring and cooled to 0°. At this temperature there is added dropwise within 45 minutes the above −15° cold dichloromethane solution of the acid chloride and the mixture is maintained at a pH-value of 7.8–8.0 by simultaneous dropwise addition of 2N sodium hydroxide via autotitrator. The mixture is subsequently stirred for a further 30 minutes at 5° and for 1 hour at 20°. 500 ml of n-butanol and 500 ml of under suction. The substance is dissolved in ca 800 ml of acetone while stirring, filtered, treated with 200 ml of butyl acetate and evaporated in vacuo to ca 300 ml, whereby the substance precipitates. It is filtered off under suction, washed with butyl acetate, hexane and petroleum ether and dried. There is obtained (6R,7R)--7-[2-(chloroacetamido-4-thiazolyl)-2-[(Z)-methoxyimino]acetamido]-3-[[2,5-dihydro-2,6-dimethyl-5-oxo-as-triazin-3-yl)-thio]methyl]-8-oxo-5-thia-1-azabicyclo[4.2.0]oct-2-ene-2-carboxylic acid, m.p. 162°–164° dec. $[\alpha]_D^{25} = -272.2°$ (c=1 in dimethylformamide). dichloromethane are added to the solution, the mixture is adjusted to a pH-value of 3 with citric acid, stirred at this pH-value for 5 minutes and the whole is filtered in vacuo. The organic phase is separated, washed 3 times with 200 ml of water each time, treated with active charcoal, filtered and evaporated at 55° in vacuo to a volume of 100 ml. It is mixed with 300 ml of ether and the precipitate is filtered off under suction.

EXAMPLE 3

Methylene (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylate pivalate 8 g of (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid sodium salt are dissolved in 80 ml of dimethylformamide, cooled to 0°, treated with 6 g of pivaloyloxymethyl iodide and stirred at 0° for 30 minutes. The solution is precipitated in ice/water, the precipitate is filtered off in vacuo, dissolved in ethyl acetate with addition of some methanol, washed with sodium hydrogen carbonate solution and sodium chloride solution, dried with magnesium sulphate and evaporated in vacuo up to the beginning of crystallisation. The crystallisation is completed by addition of a mixture of ether-petroleum ether 1:1. The substance is filtered off and subsequently chromatographed over silica gel with benzene/methanol 4:1. The uniform fractions are combined, evaporated in vacuo and finally crystallised from chloroform/ether. There is obtained methylene (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylate pivalate. M.p.=149° dec., $[\alpha]_D^{25} = -173°$ (c=1 in dimethylformamide).

EXAMPLE 4

Methylene (6R,7R)-7-[2-(2-amino-4-thiazolyl)-2-[(Z)-methoxyimino]acetamido]-3-[[(2,5-dihydro-2,6-dimethyl-5-oxo-as-triazin-3-yl)thio]methyl]-8-oxo-5-thia-1-azabicyclo[4.2.0]oct-2-ene-2-carboxylate pivalate 5.7 g of (6R,7R)-7-[2-(2-amino-4-thiazolyl-2-[(Z)-methoxyimino]acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylic acid sodium salt are treated in 30 ml of dimethylformamide at 0° with 4 g of pivaloyloxymethyl iodide and stirred at 0° for 30 minutes. The solution is precipitated in ice/water and the precipitate is filtered off in vacuo. The substance is dissolved in ethyl acetate, washed with sodium hydrogen carbonate solution and sodium chloride solution, dried over magnesium sulphate, evaporated in vacuo and mixed with ether. The solid substance is chromatographed over silica gel with benzene/methanol 85:15. The uniform fractions are combined, evaporated up to the beginning of crystallisation, mixed with ether and filtered off under suction. There is obtained methylene (6R,7R)-7-[2-(2-amino-4-thiazolyl)-2-[(Z)-methoxyimino]acetamido]-3-[[2,5-dihydro-2,6-dimethyl-5-oxo-as-triazin-3-yl)thio]methyl]-8-oxo-5-thia-1-azabicyclo[4.2.0]oct-2-ene-2-carboxylate pivalate, m.p. from 146° dec., $[\alpha]_D^{25} = -214°$ (c=1 in dimethylformamide).

EXAMPLE 5

Manufacture of dry ampoules for intramuscular administration:

A lyophilisate of 1 g of the active substance is manufactured in the customary manner and filled into an ampoule. Prior to the administration, the lyophilisate is treated with 2.5 ml of a 2% aqueous lidocaine hydrochloride solution.

What is claimed:

1. A compound of the formula

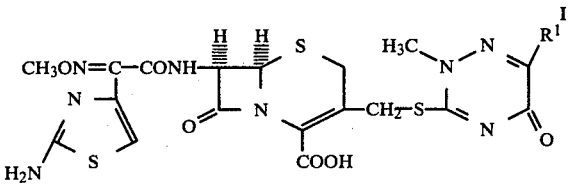

wherein $R^1$ is hydrogen and the salts thereof and hydrates thereof wherein the compound is in the syn-isomeric form or mixtures in which the syn-isomeric form predominates.

2. The compound: (6R,7R)-7-[2-(2-amino-4-thiazolyl)-2-[(Z)-methoxyimino]acetamido]-3-[[(2,5-dihydro-2-methyl-5-oxo-as-triazin-3-yl)thio]methyl]-8-oxo-5-thia-1-azabicyclo[4.2.0]oct-2-ene-2-carboxylic acid and the salts thereof and hydrates of the compound or its salts.

3. A compound of the formula

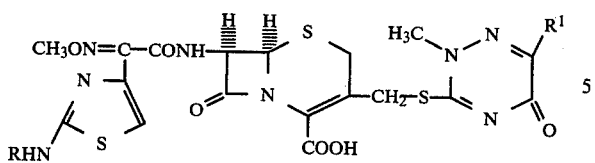

wherein $R^1$ is hydrogen and R is a cleavable protecting group selectable from the group consisting of t-butoxy carbonyl, trityl, trifluoroacetyl, bromoacetyl iodoacetyl and chloroacetyl and the carboxy group may be protected as a readily cleavable or hydroxylable ester or by salt formation.

4. A pharmaceutical preparation for the treatment and prophylaxis of infectious diseases, which comprises an effective amount of a compound of the formula

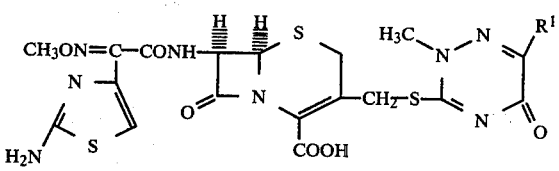

wherein $R^1$ represents hydrogen or a readily hydrolysable ester or a salt thereof or a hydrate thereof and a medicinally compatible carrier.

* * * * *